United States Patent
Haworth et al.

(10) Patent No.: US 9,776,778 B2
(45) Date of Patent: Oct. 3, 2017

(54) DEVICE FOR EMPTYING A CANISTER

(75) Inventors: Brian Haworth, Voorburg (NL); Thomas Mai, Monheim (DE)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 14/372,204

(22) PCT Filed: Mar. 2, 2012

(86) PCT No.: PCT/EP2012/053665
§ 371 (c)(1),
(2), (4) Date: Jul. 14, 2014

(87) PCT Pub. No.: WO2013/127468
PCT Pub. Date: Sep. 6, 2013

(65) Prior Publication Data
US 2014/0332554 A1   Nov. 13, 2014

(51) Int. Cl.
B67D 7/06 (2010.01)
B65D 51/16 (2006.01)
A61M 1/00 (2006.01)
B65D 47/00 (2006.01)

(52) U.S. Cl.
CPC ........... *B65D 51/16* (2013.01); *A61M 1/0005* (2013.01); *B65D 47/00* (2013.01)

(58) Field of Classification Search
CPC  B65D 47/243; B65D 47/061; B65D 51/1644; B65D 55/16; B65D 77/283; B65D 51/16; B65D 47/00; B05B 7/2408; A61M 1/0005
USPC ......... 222/23, 153.09, 484, 481.5, 478, 480, 222/566, 567, 524, 522, 525, 490, 464.1, 222/400.7, 400.8, 547, 510–514, 503; 215/306, 388, 311
See application file for complete search history.

(56) References Cited

U.S. PATENT DOCUMENTS

| | | | | |
|---|---|---|---|---|
| 2,779,517 A | * | 1/1957 | Beall, Jr. ....................... | 222/484 |
| 2,853,210 A | * | 9/1958 | Cooprider et al. ........... | 222/207 |
| 3,228,413 A | * | 1/1966 | Stevens, Jr. .......... | B67D 1/0831 |
| | | | | 137/322 |
| 3,348,736 A | * | 10/1967 | Dawes ........................... | 222/38 |

(Continued)

FOREIGN PATENT DOCUMENTS

| | | |
|---|---|---|
| DE | 4303668 A1 | 8/1994 |
| WO | 0012403 A1 | 3/2000 |
| WO | 0192133 A2 | 12/2001 |

OTHER PUBLICATIONS

International Patent Application No. PCT/EP2012/053665, International Search Report & Written Opinion mailed Aug. 2, 2012, 7 pages.

*Primary Examiner* — Lien Ngo
(74) *Attorney, Agent, or Firm* — Fredrikson & Byron, P.A.

(57) ABSTRACT

The present invention relates to a device (10) for emptying a canister (12) with a nozzle (14) with a first opening (16), comprising an adapter (18) to be at least partially arranged inside the nozzle (14), in particular inside the first opening (16), a connector (34) connectable to the adapter (18) for connecting a suction machine to the adapter (18), and a reclosable fitment (36) comprising a first fitment part (38) and a second fitment part (40), wherein the first fitment part (36) is arranged on the adapter (18) and the second fitment (40) part is arranged on the connector (34). Thus, the safety of handling an emptied canister (12) with a residue fluid may be increased.

12 Claims, 4 Drawing Sheets

(56) References Cited

U.S. PATENT DOCUMENTS

| | | | | |
|---|---|---|---|---|
| RE27,626 E | * | 4/1973 | Johnston | B67D 1/0832 |
| | | | | 222/400.7 |
| 3,726,442 A | * | 4/1973 | Davidson et al. | 222/207 |
| 4,108,336 A | * | 8/1978 | Anderson, Jr. | 222/148 |
| 4,162,749 A | * | 7/1979 | Bennett | 222/633 |
| 4,436,125 A | * | 3/1984 | Blenkush | F16L 37/0841 |
| | | | | 137/797 |
| 4,445,539 A | * | 5/1984 | Credle | B65D 83/0055 |
| | | | | 137/614.03 |
| 4,807,785 A | * | 2/1989 | Pritchett | 222/442 |
| 4,821,924 A | * | 4/1989 | Kozam | 222/211 |
| 4,832,237 A | * | 5/1989 | Hurford, Jr. | 222/464.1 |
| 5,031,801 A | * | 7/1991 | Osgar | B67D 7/0294 |
| | | | | 222/153.01 |
| 5,102,010 A | * | 4/1992 | Osgar | B65D 47/36 |
| | | | | 222/1 |
| 5,255,819 A | * | 10/1993 | Peckels | 222/1 |
| 5,318,197 A | * | 6/1994 | Martindale et al. | 222/1 |
| 5,404,901 A | * | 4/1995 | Pickrell | B67D 7/0294 |
| | | | | 137/322 |
| 6,206,240 B1 | * | 3/2001 | Osgar | B67D 7/0255 |
| | | | | 222/389 |
| 2007/0114202 A1 | * | 5/2007 | Lee | 215/311 |
| 2010/0038378 A1 | * | 2/2010 | Gabler et al. | 222/23 |
| 2010/0089950 A1 | * | 4/2010 | Helf et al. | 222/153.09 |
| 2012/0104029 A1 | * | 5/2012 | Haas | B67D 7/0294 |
| | | | | 222/1 |

* cited by examiner

DEVICE FOR EMPTYING A CANISTER

TECHNICAL FIELD OF THE INVENTION

This invention relates to a device for emptying a canister with a nozzle with a first opening, wherein the device comprises an adapter, a connector and a reclosable fitment for emptying the canister.

BACKGROUND OF THE INVENTION

Devices and systems for emptying canisters filled with a substance, in particular a fluid, are known in practice in various forms. These known devices often incorporate a suction lance that is inserted into the canister and that is pointing from an opening of the canister into the canister for drawing the substance out when coupled to a suction device. The canisters are usually not emptied by way of the suction lances so as to be free of residue, hence a residual quantity of substance, in particular fluid, remains in the container. For the disposal of canisters that are filled with dangerous or harmful substances for example it is a desirable aim to reduce the amount of substance that is left in the canister to a minimum. Moreover, it is desirable to reduce the risk of an unintended contact of a person handling the empty canisters with the substance left in the canister in order to reduce and avoid any health risks.

SUMMERY OF THE INVENTION

It is therefore an object of the present invention to provide a device for emptying a canister which reduces the risk of a contact with any substance left in the emptied canister.

This object is solved by a device for emptying a canister according to claim 1 of the present invention.

Accordingly, a device for emptying a canister with a nozzle with a first opening, comprises an adapter to be at least partially arranged inside the nozzle, in particular inside the first opening, a connector connectable to the adapter for connecting a suction machine to the adapter, and a reclosable fitment comprising a first fitment part and a second fitment part, wherein the first fitment part is arranged on the adapter and the second fitment part is arranged on the connector.

The nozzle of the canister may be arranged in a top part of the canister, wherein the nozzle comprises a first opening, preferably of a circular shape. An adapter comprising a second opening may be arranged at least partially inside the first opening of the nozzle. The adapter may be permanently arranged and/or attached in the first opening and/or the nozzle. The device further comprises a connector which on one end may be connectable to a suction machine, wherein the other end is connectable to the adapter for connecting the suction machine to the adapter and/or the nozzle and hence the canister in order to draw a fluid from the canister when the suction machine is switched on. The connector may comprise a shape matching the shape of the nozzle and/or the adapter, in order to for example connect to the nozzle and/or the adapter by overlapping. Further, the device comprises a reclosable fitment with at least a first fitment part and a second fitment part, wherein the first fitment part is arranged on the adapter and the second fitment part is arranged on the connector. The second fitment part arranged on the adapter may comprise a tube-like shape which may be inserted into the first fitment part when connecting the connector to the adapter and/or nozzle. The first fitment part and the second fitment part are, in a connected state, fluid permeable in order to allow a fluid from the canister to be drawn through the fitment towards the suction machine. The first fitment part may be arranged inside the second opening of the adapter inside the first opening of the nozzle. The first fitment part may comprise an element which may be moveably arranged at an end of the first fitment part facing towards the inside of the canister. In a closed position the element closes the first fitment part and the second opening fluid impermeable. The element of the first fitment part may be moved from the closed position into an opened position by the second fitment part when connecting the connector to the adapter and/or the nozzle of the canister. The element may be axially displaced along a symmetrical axis of the first fitment part towards the inside of the canister by the second fitment part, thus moving the element from the closed position to the opened position. The second fitment part may comprise at least one opening through which in the opened position of the element the second fitment part may be fluid permeable connected to the second opening and the inside of the canister. When the suction machine is operating, the fluid from the inside of the canister may be drawn through the second opening passed the element of the first fitment part, which may be in the opened position, through at least the one side opening into the second fitment part and into the suction machine. The element of the first fitment part is held in the opened position by the second fitment part in particularly against the underpressure of the suction machine. The element of the first fitment part may be connected to the second fitment part by positive locking. When disconnecting the connector from the adapter and/or the nozzle of the canister the second fitment part retracts the element of the first fitment part axially from the opened position into the closed position, wherein the element of the first fitment part is fixed, in particularly locked for example by a positive locking, in the closed position. The element may also be held in the closed position by a force, for example a closing force from holding part 43, attaching the element to the rest tube-like part of the first fitment part. Thus, when the connector is disconnected from the adapter and/or the nozzle the first fitment part, in particularly with the element in the closed position, remains in the adapter closing the second opening fluid impermeable. Thus, after usage a closed and sealed canister is provided, safely enclosing any remaining substance inside the canister. The reclosable fitment has the advantage that a canister with a device according to the invention may be connected and disconnected to a connector, and in particularly a suction machine, without the risk of residue fluid leaving the canister, avoiding any unintentional spillage of the fluid. Thus a device for emptying a canister is provided, enabling a safe operating of a suction machine due to a closed, reclosable device and system being used. Further a removal of a suction lance from the canister is not necessary anymore, further reducing the risk of a user of the device and canister coming into contact with a residue liquid remaining in the canister, increasing the safety of handling an emptied canister.

According to a preferred embodiment of the invention, the adapter is connectable to the outside of the nozzle, in particular by positive locking means. The adapter may extend at least partially on the inside of the nozzle in particularly the first opening. The adapter may be at least partially arranged on, in particular around, the outside of the nozzle. Between the adapter and the nozzle a sealing ring may be provided, preferably arranged inside the first opening. The adapter may be connected to the outside of the nozzle by positive locking, wherein the nozzle may comprise a part of the positive locking and the adapter enclosing the outside of the nozzle may comprise the corresponding part of the positive locking. The positive locking is preferably designed in a non-detachable form as an anti pilfering means of the adapter. This has the advantage, that the canister may be sealed with the adapter and that the adapter may not be removed.

According to an embodiment of the invention, the connector is detachably connectable to the adapter, in particular by positive locking. For connecting the connector detachably to the adapter, in particularly to the outside of the adapter, the connector may comprise a locking device. The locking device may be designed as a detachable snap fit connector. The connector with the detachable snap fit may be attached to the adapter by snapping the connector over the adapter, wherein the snap fit locking device safely secures the connector in place during operation, for example of a suction machine. For detaching the connector from the adapter the locking device, or at least a part of the locking device, may be axially displaced, in particularly by sliding the locking device in the direction of the release of the connector, whereby the locking device unlocks and allows for removing the connector from the adapter. Attaching the connector to the adapter has the advantage that a standard canister may be used in order to reduce manufacturing costs. Further, an adapter may be chosen according to the fluid to be filled into the canister, allowing for a matching connection between an adapter and a corresponding connector, so that only a defined connector may be attached to the corresponding adapter, reducing the risk of a connector being attached to a canister with a wrong fluid, increasing the safety of handling the canisters.

According to an embodiment of the invention, the adapter and the connector comprise a profiling. The adapter, in particularly the outside of the adapter, and the connector may comprise a matching profiling in order to ensure that only defined pairings of an adapter with a connector may be used. The profiling may differ, for example according to the type of fluid inside the canister. The profiling on the adapter, in particularly on the outside of the adapter covering the nozzle, may be circumferentially arranged, providing a regular or an irregular pattern of a tongue and groove like connection for connecting a matching connector to the corresponding adapter. Different profilings may be provided wherein certain profilings correspond to certain fluids. This has the advantage, that the risk of attaching a connector to a canister with a wrong fluid may be reduced.

According to an embodiment of the invention, the adapter comprises a degassing means. The adapter may comprise a degassing means which may be impermeable to fluids, allowing a gas to pass through the degassing means in order to keep a pressure, for example during storage, inside the canister stable. The degassing means may be designed in form of a membrane. This has the advantage, that the risk of the canister being damaged due to a high gas pressure may be reduced.

According to a preferred embodiment of the invention, the adapter comprises a venting means. The venting means is for venting the inside of the canister, for example when the canister is connected to a suction machine and when a fluid is drawn out of the canister. The venting means may be designed in form of a membrane and/or a valve, in particularly a spring-biased valve. The spring-biased valve may be designed in form of a check valve. Further the connector may comprise a venting hole for venting which optimizes the venting of the canister in a connected state of the connector. Thus, the drawing of a fluid out of the canister may be improved.

According to a preferred embodiment of the invention, the connector comprises a pin-shaped element on the inside of connector facing the adapter for operating the venting means. The pin-shaped element of the connector may be arranged on the inside of the connector facing the adapter, for example prior to connecting the connector to the adapter. The pin-shaped element may be eccentrically arranged on the connector. The venting means in the adapter may also be eccentrically arranged. The venting means may be activated by the pin-shaped element of the connector when the connector is connected to the adapter and/or the nozzle. The pin-shaped element may open the venting means in form of a venting valve, in particularly a spring-based valve, by pushing back the valve against the spring thus opening the valve and allowing, for example, air to reach the inside of the canister. This allows for a simple designed venting means which allows for a save and fluid impermeable storage of the canister.

According to an embodiment of the invention, the device further comprises an empty alarm, in particular arranged on the connector. The empty alarm may for example be arranged on the connector in order to monitor the presence and/or lack of the substance. The empty alarm may be induction-based. The empty alarm is to indicate that the fluid in the canister is used up, for example to the suction machine, in order to stop a pump or indicate the need for changing the canister to an operator.

According to a preferred embodiment of the invention, the connector comprises a cavity and a flow body, wherein the flow body is moveably arranged inside the cavity. The cavity and the flow body may be part of the reclosable fitment. The cavity of the connector may be arranged on the side of the connector facing towards the suction machine. When the suction machine is working the fluid may be drawn from the canister displacing the flow body axially, flowing around the flow body through the cavity towards the suction machine. The cavity may be fluid permeable connectable to the second opening on one end and to the suction machine on the other end. The flow body may, for example, be designed in form of a float, in particular comprising ribs in order to allow a fluid to flow pass the flow body and displace the flow body. In particularly with an induction-based empty alarm the flow body may be designed as a float, in particular as an at least partially metallic float, arranged inside the cavity next to an electromagnetic coil or an electromagnet. If a pump of a suction machine is not operating and drawing the fluid from the canister the electromagnet may attract the float, sealing for example the connector fluid impermeable. When the pump is switched on and working, the electromagnet may be switched off or may reverse its polarity or exert a lower force of attraction onto the float, allowing the float to move away from the electromagnet and the electromagnetic field, thus allowing a fluid to flow through the cavity around the float. A flowing substance may move the float, in particular in a downstream direction towards the suction machine, away from the electromagnet. This movement of the float may be detected, thus indicating the flow and the presence of the fluid, for example, by altering the magnetic field of an active electromagnet. If the fluid runs out the float may drop back towards the electromagnet, indicating the lack of fluid, for example, by altering the magnetic field of the electromagnet by reducing the distance towards the electromagnet, which may trigger the empty alarm. The electromagnet may be switched on, reverse its polarity again or increase the attraction force exerted onto the float in order to attract the float towards the electromagnet, hence sealing the cavity and thus the connector fluid impermeable, avoiding fluid to leak from the cavity. Thus, the suction machine, in particular the suction pump, may be stopped and an alarm be sounded when the fluid runs out and the canister is emptied.

According to an embodiment of the invention, the device further comprises a rinsing coupling connectable to a rinsing fluid supply. The rinsing coupling may be arranged inside the adapter and/or the connector, and may be connectable, for example, to a rinsing fluid supply, for example, a water supply. The adapter may comprise a third opening for allowing the rinsing fluid to pass through the adapter into the inside of the canister. The rinsing coupling allows for rinsing or flushing the inside of the canister, thus reducing the concentration of any fluid left inside the canister after disconnecting the canister from a suction machine.

According to a further embodiment of the invention, the device further comprises an indicator switch. The indicator switch may be arranged on the connector. The indicator switch may, for example, comprise a metal stripe and a pin, wherein the pin is arranged in such a way, that when the connector is mounted properly to the adapter, the pin contacts the adapter and pushes the metal stripe into contact with a metal contact inside the connector for example, closing an electric circuit. Thus the proper mounting of the connector to the adapter may be indicated, in order to start the suction machine in order to draw the fluid out of the canister. The metal stripe moved by the pin may also activate a switch, indicating the proper mounting of the connector. Thus, the operating of the securely connected connector may be provided.

According to an embodiment of the invention, the adapter comprises a suction lance attached to the second opening of the adapter. The adapter may comprise a suction lance attached to the adapter, in particular to the second opening of the adapter. Thus the second opening may be connected fluid permeable to the inside of the canister via the suction lance enabling a fluid to be drawn out of the canister via the suction lance and the second opening towards the suction machine. The suction lance and the adapter may be designed as a one-piece form. The suction lance may extend into the canister in particularly to a bottom part contacting the bottom part.

According to a further embodiment of the invention, the device comprises a cover cap. The cover cap may be plugged into the second opening of the adapter and may comprise a seal in order to close the second opening fluid impermeable. The cover cap may also cover the first opening of the nozzle, the venting means inside the adapter and/or the rinsing coupling arranged on the adapter. The cover cap may avoid a pollution of the adapter, in particularly of the second opening of the adapter, thus increasing the reliability of the device.

A further aspect of the present invention is a suction system comprising a device for emptying a canister as previously described.

The afore mentioned components, as well as the claimed components and the components to be used in accordance with the invention in the described embodiments, are not subject to any special exceptions with respect to their size, shape, material selection and technical concept such that the selection criteria known in the pursuant field can be applied without a limitation.

BRIEF DESCRIPTION OF THE DRAWINGS

Additional details, features, characteristics and advantages of the object of the invention are disclosed in the subclaims, the figures and the following description of the respective figures and examples, which
in exemplary fashion—show several embodiments and examples of a canister and a connector closure according to the invention.

In the drawings.

Figure 1:
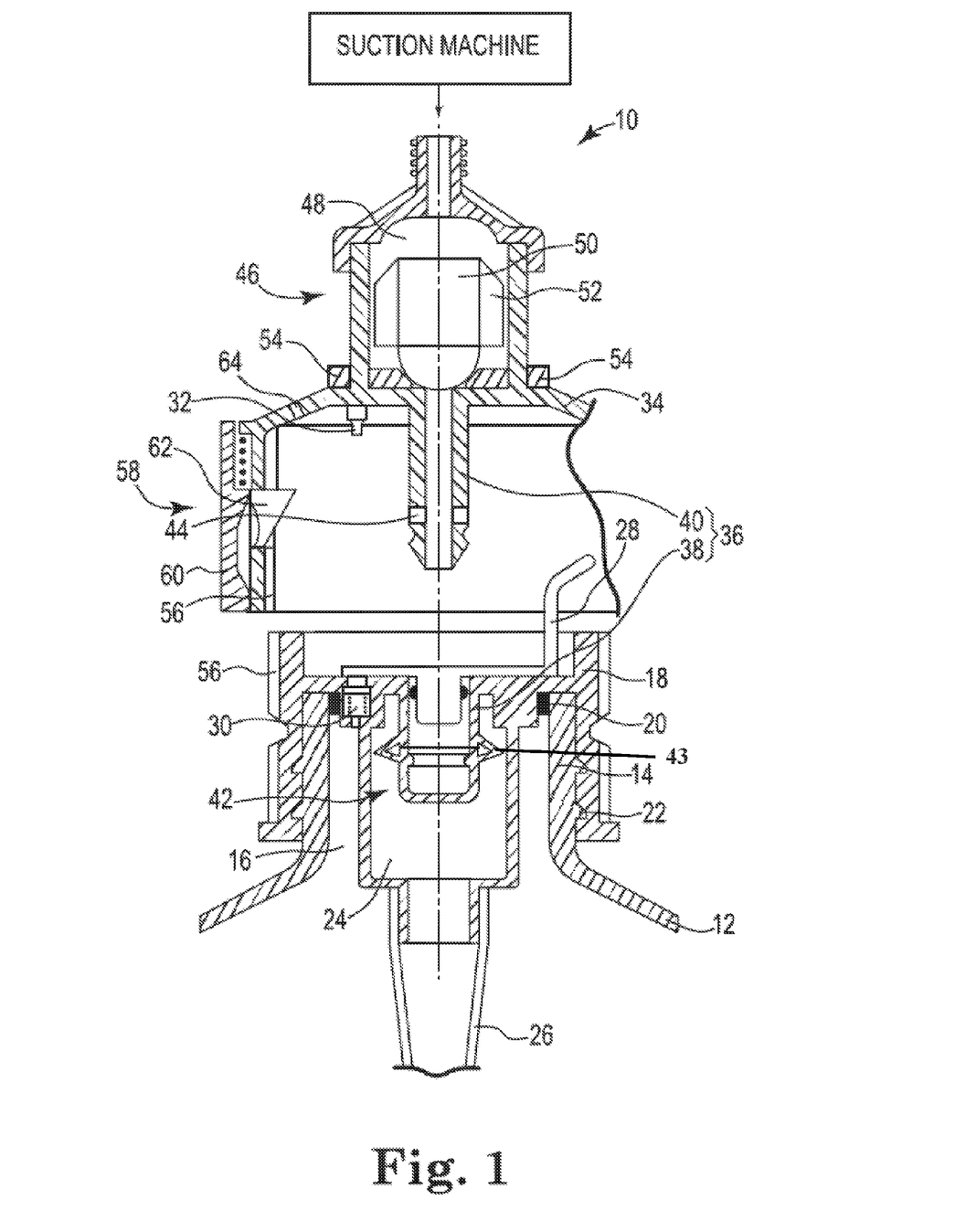
FIG. 1 is an illustration of a device constructed in accordance with the invention.

The illustration in FIG. 1 shows a device 10 for emptying a canister 12 with a nozzle 14 and a first opening 16 in a disconnected state. An adapter 18 is arranged on the nozzle 14 of the canister 12, wherein the adapter 18 extends along the outside of the nozzle 14 and partially inside the nozzle 14, in particular the first opening 16. A sealing ring 20 is arranged in between the adapter 18 and the inside of the nozzle 14. The adapter 18 is attached to the nozzle 14 by positive locking means 22, wherein the positive locking means 22 is designed in a non-pilfering form. The adapter 18 comprises a second opening 24 which is arranged centrally on the adapter 18 and is extended into the inside of the canister 12 by a suction lance 26, which is attached to the adapter 18 connecting the second opening 24 fluid permeable to the inside of the canister 12. The second opening 24 inside the adapter 18 is covered by a cover cap 28, which is plugged into the second opening 24, sealing the second opening 24 with a seal in order to avoid pollution, for example, during the storage and/or transportation of the canister 12 with the attached adapter 18. The cover cap 28 also covers a venting means 30, which is arranged eccentrically to the second opening 24 in the adapter 18. The venting means 30 is designed in form of a valve, in particularly a spring-biased check valve. A venting means 30 may be operated by a pin-shaped element 32 which is attached to the inside of a connector 34. The connector 34 is shown in a disengaged position next to the adapter 18. The device 10 comprises a reclosable fitment 36, comprising a first fitment part 38 and a second fitment 40. When connecting the connector 34, which may be connected to a suction machine (not shown), in particular the second fitment part 40 may be plugged into the first fitment part 38, whereby an element 42 of the reclosable fitment 36, particularly the first fitment part 38, may be displaced, in particular within the second opening 24, towards the inside of the canister 12, whereby the fluid may be sucked towards the suction machine. In order to provide a fluid permeable connection through the reclosable fitment 36, the second fitment part 40 comprises openings 44 through which the fluid may be drawn from the canister 12 when the reclosable fitment 36, in particularly the second fitment part 40 with the element 42, is in an opened position. The connector 34 comprises an empty alarm 46, which is arranged on a side of the connector 34 facing the suction machine. The empty alarm 46 comprises a cavity 48 in which a flow body 50 in form of a float is arranged. The flow body 50 is shown in a position sealing the cavity 48. The flow body 50 comprises several ribs 52 in order to provide a minimum distance between the flow body 50 and the inside of the cavity 48 in order to allow a fluid to flow past the flow body 50, when the suction machine is operating and a fluid is drawn from the canister 12 through the cavity 48. The flow body 50 is arranged next to a ring-shaped electromagnet 54 which is arranged inside and outside of the cavity 48. Depending on the movement and/or the position of the flow body 50 a presence or absence of a fluid within the cavity 48 may be detected by the empty alarm 46. When connecting the connector 34 to the adapter 18, the cover cap 28 is removed and the connector 34 snapped onto the adapter 18. The connector 34 and the adapter 18, particularly on the outside of the adapter 18, comprise a profiling 56 in order to ensure that only defined connectors 34 are connectable to corresponding defined adapters 18. In order to secure the connector 34 to the adapter 18, in particularly detachable, the connector 34 comprises a locking device 58. The locking device 58 comprises a form locking element 62 which protrudes towards the inside of the connector 34 interlocking into a corresponding recess on the outside of the adapter 18 in a connected state of the connector 34. The form locking element 62 may be elastically displaced towards the inside of the connector 34 by an outer ring 60, which is spring-biased and may be slid towards a disconnecting direction of the connector 34, allowing the form locking element 62 to move outwards, out of the recess in the adapter 18, in order to release the connector 34. The connector 34 further comprises a venting hole 64 in order to allow air to be drawn towards the venting means 30, in particularly in a connected state of the connector 34 when fluid is being drawn from the canister 12.

Figure 2:
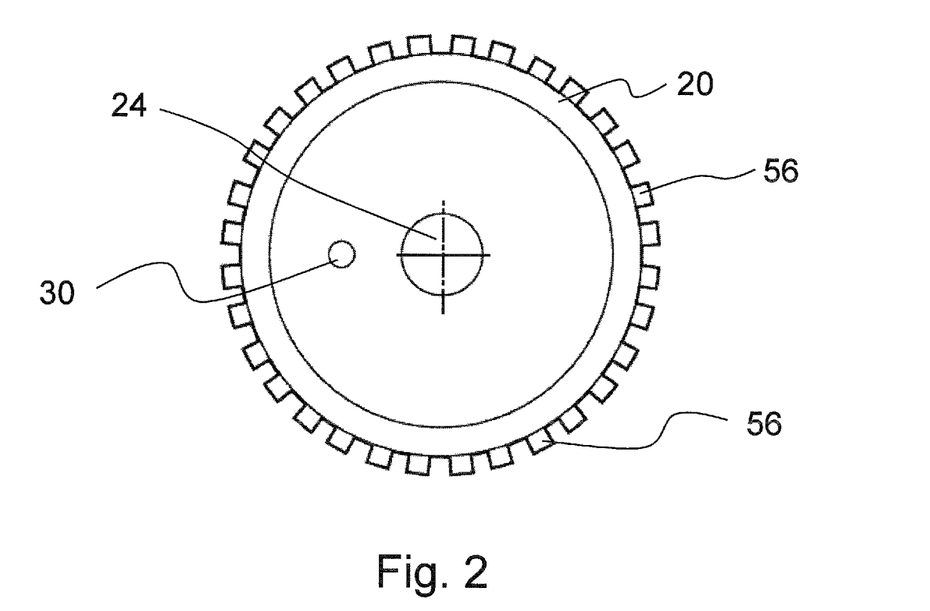
FIG. 2 is a schematic top view of an adapter comprising a profiling in accordance with the invention.
Figure 3:
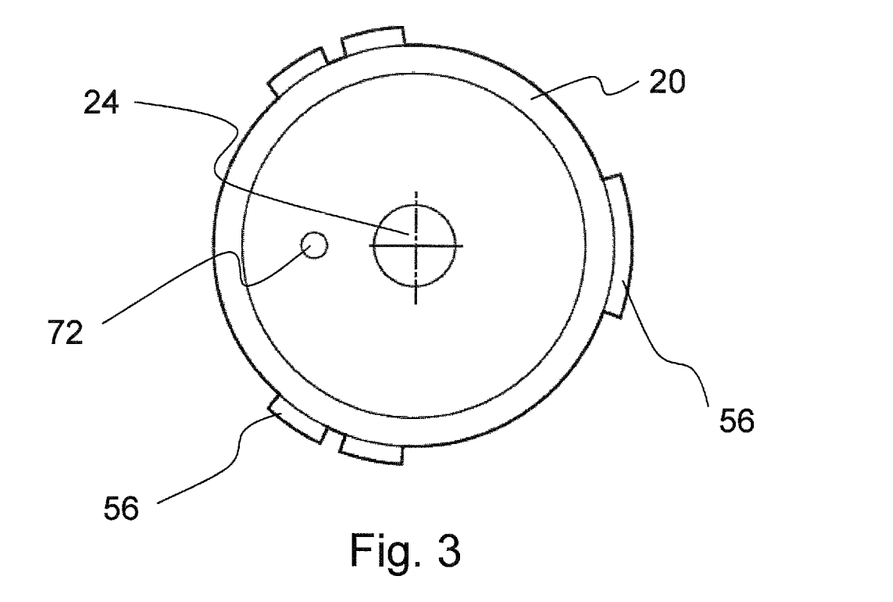
FIG. 3 is a top view of the adapter shown in FIG. 2 in accordance with the invention comprising an irregular profiling.

The adapter 18 shown in FIG. 2, comprises a centrally arranged second opening 24 and an eccentrically arranged venting means 30. The adapter 18 comprises on the outside a profiling 56, matching the profiling (not shown) of a connector (not shown) corresponding to the adapter 18. The profiling 56 of the adapter 18 is, as an example, circumferentially arranged, in a regular pattern, providing a tongue and groove like connection for connecting a connector to the allocated corresponding adapter 18. The profiling 56 shown in FIG. 3 is, as an example, arranged on the outside of the adapter 18 and comprises smaller and larger circumferentially arranged tongue-like connections of a tongue and groove like connection for connecting the adapter 18 to an allocated connector (not shown). A degassing means 72 is shown in an eccentrically position on the adapter 18. Thus, an irregular pattern of the profiling 56 is provided, in order to ensure that only a certain defined connector may be connected to the corresponding adapter 18.

Figure 4:
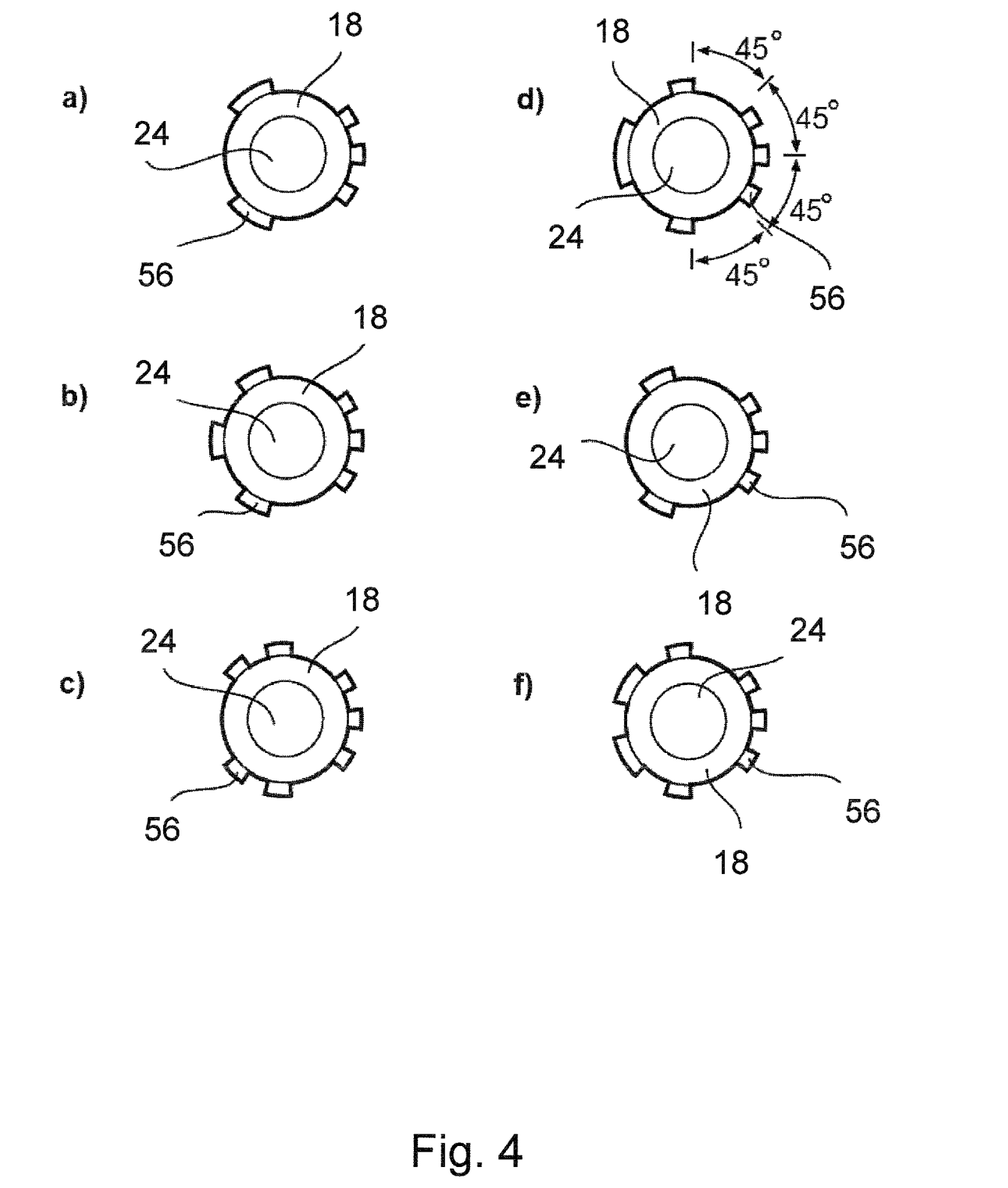
FIG. 4 is an illustration of profiling, comprising six different forms from a) to f) constructed in accordance with the invention.

The profiling 56 may be designed in any number of designs. In FIG. 4 six different profilings 56 a) to f) are illustrated as an example. The profiling 56 on the outside of the adapter 18 may be arranged in different patterns, comprising smaller and larger circumferential tongue-like sections of a tongue and groove connection for connecting a connector (not shown) to the allocated adapter 18, like a lock-and-key system. The patterns of the profiling 56 may be arranged in such a way, that in several sections of 45° each, none, one, two or two and a half patterns may be arranged. The tongue-like patterns 56 extend along the outside of the adapter 18, essentially in parallel to a symmetrical axis of the adapter 18 and/or opening 24 or nozzle (not shown).

Figure 5:
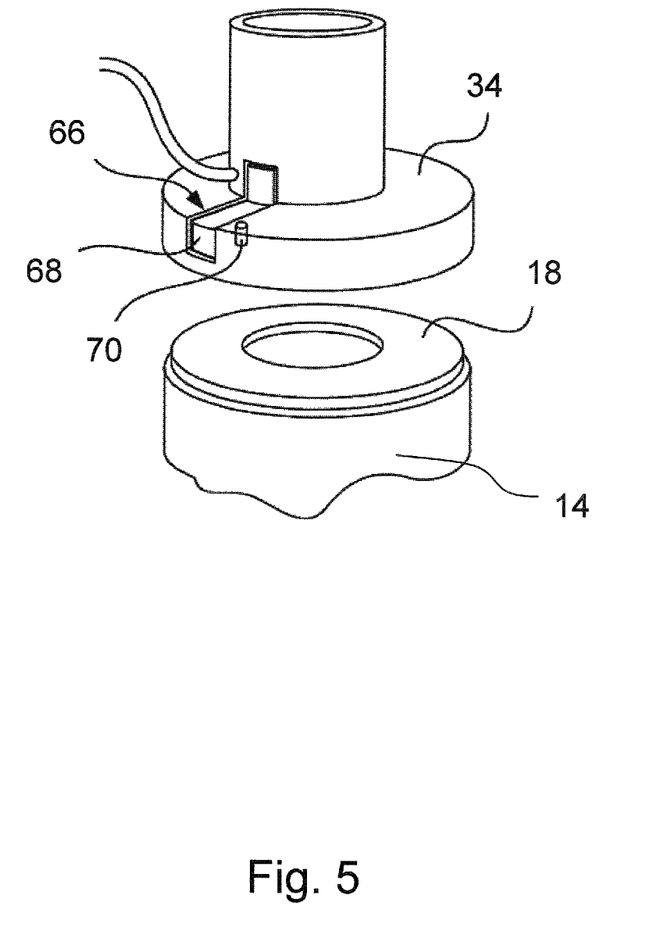
FIG. 5 is a schematic perspective of an indicator switch constructed in accordance with the invention.

In FIG. 5 an adapter 18 is shown arranged partly inside a nozzle 14, with a connector 34 shown in a disengaged position. The connector 34 comprises an indicator switch 66 with a stripe 68 and a pin 70, wherein the pin 70 may push the stripe 68 towards a contact (not shown) when the connector 34 is mounted properly to the adapter 18 and/or the nozzle 14. The pin 70 may extend out of the connector 34 towards the canister 12 and/or towards the adapter 18. The pin 70 arranged at the connector 34 may be displaced by the adapter 18 when the connector is connected to the adapter 18 and/or the nozzle 14 of the canister 12. By moving the pin 70 the stripe 68 may be moved in order to indicate a properly attached connector 34, thus providing an indication for a properly closed device 10 for emptying a canister 12.

The particular combinations of elements and features in the above detailed embodiments are exemplary only; the interchanging and substitution of these teachings with other teachings in this and the patents/applications incorporate by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by the way of example only and is not intending as limiting. In the claims, the wording "comprising" does not exclude other elements or steps, and the identified article "a" or "an" does not exclude a plurality. The mere fact that certain measures are recited in mutually different dependent claims does not indicate that a combination of these measures cannot be used to advantage. The inventions scope is defined in the following claims and the equivalents thereto. Furthermore, reference signs used in the description and claims do not limit the scope of the invention as claimed.

LIST OF REFERENCE NUMERALS

10 device
12 canister
14 nozzle
16 first opening
18 adapter
20 sealing ring
22 positive locking means
24 second opening
26 suction lance
28 cover cap
30 venting means
32 pin-shaped element
34 connector
36 reclosable fitment
38 first fitment part
40 second fitment part
42 element
44 opening
46 empty alarm
48 cavity
50 flow body
52 rib
54 electromagnet
56 profiling
58 locking device
60 outer ring
62 form locking element
64 venting hole
66 indicator switch
68 stripe
70 pin
72 degassing means

The invention claimed is:

1. A device for emptying a canister having a nozzle defining an opening, the device comprising:

an adapter securable to the canister, the adapter at least partially arranged inside the opening of the nozzle when secured to the canister to seal the opening of the nozzle, the adapter having a first fitment part extending axially within the opening of the nozzle when the adapter is secured to the canister, the first fitment part selectively unsealing the opening of the nozzle, the first fitment part having an opening portion extending into the nozzle, an element, and a holding part, the holding part attaching the element to the opening portion; and, a connector connectable to the adapter, the connector configured for connecting a suction machine to the adapter and having a second fitment part, the element being movable from a closed position to an opened position, the element in the closed position preventing fluid from being drawn from the canister through the first fitment, the element in the opened position allowing fluid to be drawn from the canister through the first fitment, the holding part being adapted to provide a closing force to hold the element in a closed position, wherein locking of the second fitment part to the first fitment part moves the element from the closed position to the opened position in opposition to the closing force without moving the axial position of the opening portion within the nozzle, wherein the second fitment part includes radially extending openings aligned with the element when the element is in the opened position.

2. The device according to claim 1, characterised in that the adapter and the connector comprise a profiling.

3. The device according to claim 1, characterised in that the adapter comprises a degassing means.

4. The device according to claim 1, characterised in that the adapter comprises a venting means.

5. The device according to claim 4, characterised in that the connector comprises a pin-shaped element on the inside of the connector facing the adapter for operating the venting means.

6. The device according to claim 1, characterised in that the device comprises an empty alarm arranged on the connector.

7. The device according to claim 6, characterised in that the connector comprises a cavity and a flow body, wherein the flow body is moveably arranged inside the cavity.

8. The device according to claim 1, characterised in that the device comprises an indicator switch.

9. The device according to claim 1, characterised in that the adapter comprises a suction lance attached to the second opening of the adapter.

10. The device according to claim 1, characterised in that the device comprises a cover cap.

11. A suction system comprising a device for emptying a canister according to claim 1.

12. The device according to claim 1, wherein the element is configured to move axially in a direction toward an inside of the canister when moving from the closed position to the opened position, and wherein at least a portion of the second fitment part is configured to fit within the first fitment part and connect to the element to move the element from the closed to the opened position.

* * * * *